United States Patent [19]

Lyons et al.

[11] 4,225,728

[45] Sep. 30, 1980

[54] CATALYTIC PROCESS FOR THE CONVERSION OF ETHYL BENZENE TO EQUIMOLAR AMOUNTS OF VINYL ACETATE AND PHENOL

[75] Inventors: James E. Lyons, Wallingford; George Suld, Springfield; Robert W. Shinn, Aston, all of Pa.

[73] Assignee: Suntech, Inc., Philadelphia, Pa.

[21] Appl. No.: 957,274

[22] Filed: Nov. 3, 1978

[51] Int. Cl.$^2$ .................. C07C 69/15; C07C 67/28; C07C 39/04; C07C 37/00

[52] U.S. Cl. ..................... 560/261; 260/546; 560/131; 560/241; 562/542; 562/607; 568/806; 568/302; 568/320

[58] Field of Search .................. 560/261, 131, 241; 568/806; 562/607, 542; 260/585.5, 546

[56] References Cited

U.S. PATENT DOCUMENTS

| | | | |
|---|---|---|---|
| 3,652,668 | 3/1972 | Bryce-Smith et al. | 560/241 |
| 3,665,030 | 5/1972 | d'Ostrowick et al. | 560/241 |
| 3,787,485 | 1/1974 | Fernandez | 560/261 |
| 3,804,887 | 4/1974 | Hoch et al. | 560/246 |
| 3,867,430 | 2/1975 | Grozhan et al. | 560/241 |

FOREIGN PATENT DOCUMENTS

| | | | |
|---|---|---|---|
| 1960520 | 6/1971 | Fed. Rep. of Germany | 560/241 |
| 1244080 | 8/1971 | United Kingdom | 560/131 |
| 321518 | 2/1972 | U.S.S.R. | 560/131 |
| 329162 | 3/1972 | U.S.S.R. | 560/131 |

OTHER PUBLICATIONS

Grozhan et al., Doklady Akad. Nauk. SSSR, vol. 204, No. 4, pp. 872–873, Jun. 1972.

*Primary Examiner*—Vivian Garner
*Attorney, Agent, or Firm*—J. Edward Hess; Donald R. Johnson; Stanford M. Back

[57] ABSTRACT

Equimolar amounts of vinyl acetate and phenol may be prepared by oxidation of ethyl benzene. The catalytic oxidation, of ethyl benzene, when carried out in the presence of acetic anhydride, forms phenyl acetate and ethylidene diacetate. Pyrolysis of these two intermediates yields vinyl acetate and phenol.

In a further embodiment of this invention it has been found that persulfate promoters such as potassium persulfate, persulfuric acid, or Caro's dry acid are particularly effective promoters for this oxidation reaction.

21 Claims, 1 Drawing Figure

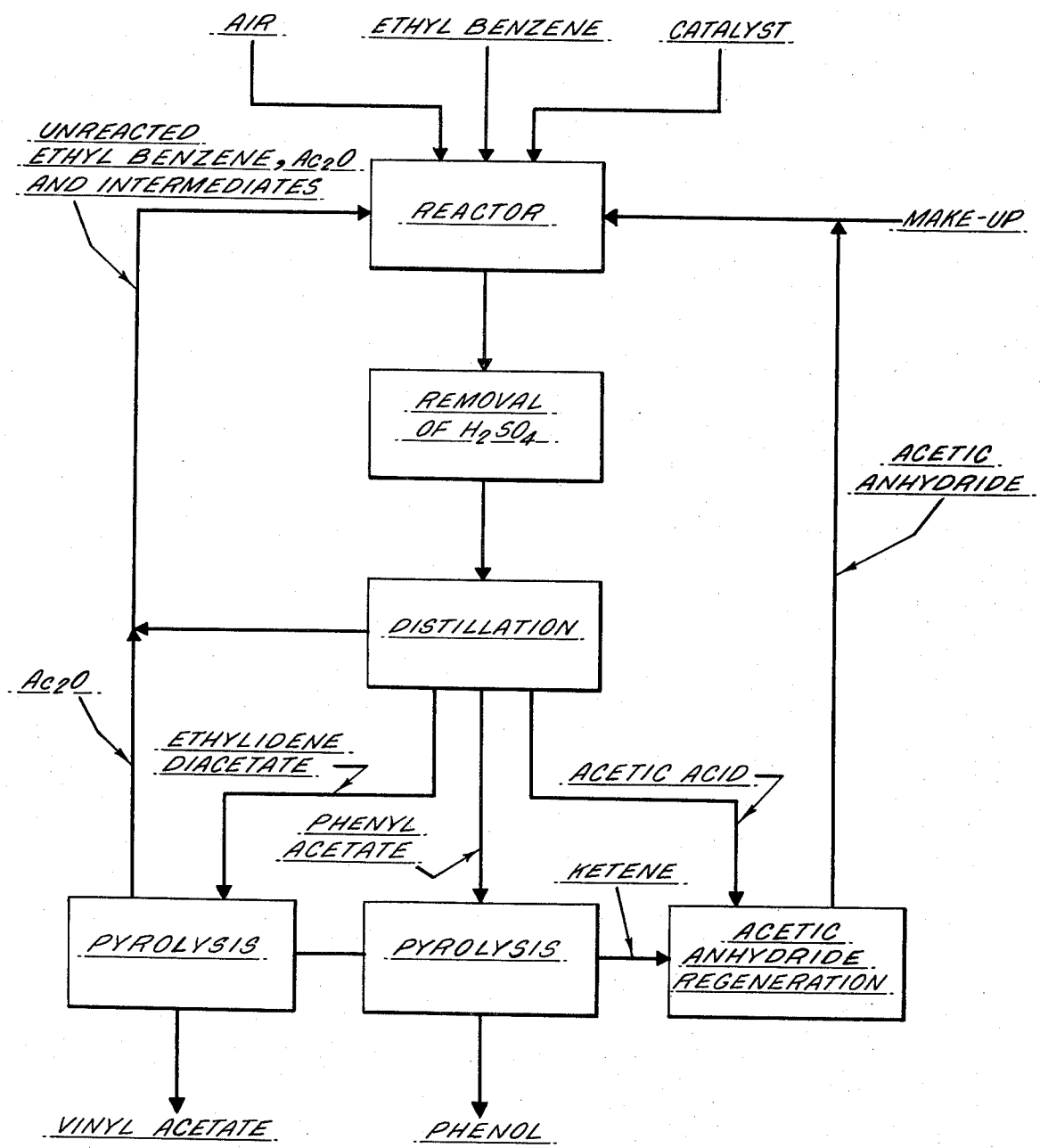

CATALYTIC PROCESS FOR THE CONVERSION OF ETHYL BENZENE TO EQUIMOLAR AMOUNTS OF VINYL ACETATE AND PHENOL

BACKGROUND OF THE INVENTION

This invention relates to a process for the oxidation of ethyl benzene. More particularly, this invention relates to a novel process for the oxidation of ethyl benzene to form vinyl acetate and phenol in equimolar amounts.

It is known from Grozhan et al, *Doklady Akad. Nauk SSSR*, 204 No. 4, page 872, and Russian Pat. Nos. 329,167 (1972) and 321,518 (1971) that when ethyl benzene is oxidized in the presence of acetic anhydride and a strong acid, followed by saponification of the total reaction product, phenol is formed in substantial quantities, together with lesser amounts of benzaldehyde, benzyl acetate and other related materials. Counterpart British Pat. No. 1,244,080, from the same Russian sources, teaches a like process and further proposes a mechanism whereby through the formation and rearrangement of a hydroperoxide intermediate, both phenol and an aliphatic aldehyde or ketone are produced.

Significantly, there is no mention or suggestion of the formation of ethylidene diacetate, and therefore obviously no teaching of converting said ethylidene diacetate to vinyl acetate. Moreover, the Russiun work is silent as to the use of any promoters or other adjuvants in addition to acid catalysts which would serve to enhance the rate, yield, or selectivity of this oxidation reaction.

SUMMARY OF THE INVENTION

In accordance with the present invention there is provided a novel process for the oxidation of ethyl benzene to ultimately yield equimolar amounts of vinyl acetate and phenol. In general, this is achieved by oxidizing ethyl benzene with air or oxygen at selected pressures and temperatures in the liquid phase in the presence of acetic anhydride and a strong acid catalyst to form phenyl acetate and ethylidene diacetate in equal amounts together with acetic acid. The ethylidene diacetate and phenyl acetate are separated by distillation of the reaction product. The phenyl acetate is then pyrolyzed to form phenol and ketene, while the ethylidene diacetate is pyrolyzed to form vinyl acetate and acetic acid. The acetic acid and ketene may then be converted to acetic anhydride by known methods and recycled to the oxidation step.

The overall equation for this novel process can be formulated as shown below:

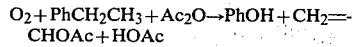

This process is also characterized by the use of certain select temperatures, pressures and promoters which further enhance the yield of the desired products.

DESCRIPTION OF THE DRAWING

FIG. 1 is a block flow diagram which shows each aspect of the overall reaction from ethyl benzene to final products.

DESCRIPTION OF THE REACTION

As aforementioned, the first step of this process is the liquid phase oxidation of ethyl benzene with a strong acid catalyst to form phenyl acetate and ethylidene diacetate. This reaction may be illustrated as follows:

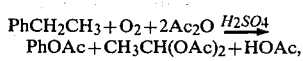

wherein the weight ratio of ethyl benzene to acetic anhydride is in the range of from about 50:1 to 1:10, and preferably 10:1 to 2:1, while the ratio of $H_2SO_4$ to ethyl benzene employed is from about $5\times10^{-4}$ to $1\times10^{-2}$, and preferably $1\times10^{-3}$ to $5\times10^{-3}$.

The reaction, which employs oxygen or equivalent amounts of air, should be carried out at temperatures in the range of from about 140° to 300° C., and preferably about 150° to 250° C., and at initial pressures of from about 50 to 450 psig. The pressure is desirably generated by charging to an autoclave air or mixtures of oxygen and nitrogen having an oxygen/nitrogen ratio of from 10:1 to 1:20 psig. The reaction mixture is then heated and the reactor pressure rises accordingly.

The reaction may be run in excess ethyl benzene as a solvent or in organic solvents such as benzene, chlorobenzene, or acetic acid. Carrying out the reaction in inert solvents such as benzene or chlorobenzene does not appreciably affect yield or selectivity but when acetic acid is employed, significantly increased selectivities may be observed. In order for rapid reactions in acetic acid promoters such as Caro's dry acid should be employed.

It has been discovered that for purposes of providing a smoothly catalyzed reaction without the formation of considerable quantities of unwanted $CO_2$ by-product, there should desirably be employed in the course of this reaction $MoO_3$. This oxide is preferably added in amounts of $10^{-3}$ to $10^{-2}$ g per gram of ethyl benzene.

In a further embodiment of this invention it has been found that persulfate promoters such as sodium persulfate, potassium persulfate, persulfuric acid, or Caro's dry acid are particularly effective promoters for the ethyl benzene oxidation reaction. These promoters are desirably used in amounts of from about $10^{-3}$ to $10^{-1}$ g per gram of ethyl benzene.

If desired, both the $MoO_3$ catalyst and the promoters may be used jointly, although this is not essential. However, enhanced results are generally obtained thereby.

The oxidation product containing phenyl acetate and ethylidene diacetate is then routinely treated to remove the acid catalyst therefrom. The phenyl acetate and ethylidene diacetate are then separated by distillation under vacuum.

The recovered phenyl acetate may then be converted to phenol and ketene by pyrolysis. This is conventionally achieved by heating the phenyl acetate at temperatures of from about 500° to 1000° C., preferably at about 625° C., preferably in the presence of a catalyst such as triethyl phosphate, and separating the effluent phenol and ketene by conventional means.

In a like manner, the pyrolysis of ethylidene diacetate yields vinyl acetate and acetic acid. This pyrolysis is conventionally carried out in one step in a cracking tower at elevated temperatures in the presence of a suitable catalyst. The ketene recovered from the phenyl acetate pyrolysis, together with the acetic acid recovered from the oxidation of the ethyl benzene may then be converted to acetic anhydride for recycling to the initial oxidation step. This is readily achieved by contacting the gaseous ketene with acetic acid at room temperature in the liquid phase.

The following examples are provided solely for purposes of illustrating but not limiting the novel process of this invention.

EXAMPLE 1

Ethyl benzene (20.0 ml), acetic anhydride (5.7 ml) and concentrated sulfuric acid (0.11 g) were charged to a 300 ml, rocking autoclave. Air (290 psi) was then added and the mixture heated to 200° C. Temperature was maintained at 200° C. for 30 minutes, the autoclave cooled and the products analyzed by standardized glpc. Ethyl benzene conversion (9.5%) was determined both by oxygen uptake and by standardized glpc analysis. Molar selectivities of the oxidation products (based on ethyl benzene consumed) are given in parenthesis: ethylidene diacetate (89%), phenyl acetate (83%), acetophenone (9%) and others (8%).

EXAMPLE 2

Ethyl benzene (20.0 ml) acetic anhydride (5.7 ml) concentrated sulfuric acid (0.11 g.), and $MoO_3$ (0.10 g) are charged to a rocking autoclave. Air (290 psi) is then added and the mixture heated to 195° C. Temperature is maintained at 195° C. for 30 minutes, the autoclave cooled and products analyzed by standardized glpc. Ethyl benzene was converted to ethylidene diacetate and phenyl acetate in good yield and high selectivity.

EXAMPLE 3

In accordance with the procedure of Example 1, but adding dry Caro's acid (0.30 g), ethyl benzene is converted to ethylidene diacetate and phenyl acetate in high selectivity.

EXAMPLE 4

In accordance with the procedures of Example 1, but adding dry Caro's acid (0.30 g) and $MoO_3$(0.10 g), ethyl benzene is converted to ethylidene diacetate and phenyl acetate in high selectivity.

EXAMPLE 5

In accordance with the procedures of Example 1, but adding dry Caro's acid (0.50 g) and acetic acid (5.7 ml), ethyl benzene is converted to ethylidene diacetate and phenyl acetate with smaller amounts of acetophenone and other by-products.

EXAMPLE 6

Pyrolysis of ethylidene diacetate to vinyl acetate and acetic acid is accomplished catalytically at about 170° C. in a known manner. Ethylidene diacetate is fed to a pyrolysis reactor at 170° C. and 1.1 atmosphere pressure in the presence of benzene sulfonic acid as a catalyst. Reaction products from the pyrolysis tower are rapidly removed overhead. The pyrolysis tower overhead is stripped of light ends and vinyl acetate (75% selectivity) is recovered by fractionation.

EXAMPLE 7

Pyrolysis of phenyl acetate to phenol and ketene is accomplished thermally at 625° C. by passing it through a well conditioned tubular reactor. The effluent is condensed to give 84% yield of phenol and 89% yield of ketene.

The reaction may be carried out at a somewhat lower temperature in the presence of triethyl phosphate catalyst at space velocities of between 900 and 1000 $hr^{-1}$. Yields in excess of 90% are obtained.

EXAMPLE 8

Gaseous ketene obtained from phenyl acetate pyrolysis reacts exothermically with acetic acid (distilled from the oxidation reaction product) in a scrubber reactor with sufficient heat removal capacity. Heat of reaction is 15 kcal/mole. The reaction is carried out in two stages at 30°-40° C. and pressures of 50-150 mm Hg. Conversions of acetic acid and ketene to acetic anhydride are 90% and 98% respectively. Selectivity to acetic anhydride exceeds 95%.

The invention claimed is:

1. A process for the oxidation of ethyl benzene to form vinyl acetate and phenol which comprises:
   (a) oxidizing ethyl benzene with air or oxygen in the liquid phase at temperatures of from 140°-300° C. and at elevated pressures in the presence of a strong acid catalyst, acetic anhydride, and molybdenum trioxide to form phenyl acetate and ethylidene diacetate in approximately equimolar amounts, together with acetic acid;
   (b) separating and recovering said phenyl acetate and ethylidene diacetate;
   (c) pyrolyzing said phenyl acetate to form phenol and ketene; and
   (d) pyrolyzing said ethylidene diacetate to form vinyl acetate and acetic acid.

2. The process of claim 1 wherein the acetic acid and ketene are converted to acetic anhydride and recycled to the oxidation step.

3. The process of claim 1 wherein the pressure in step (a) is in the range of from about 50 to 450 psig.

4. The process of claim 1 wherein the acid catalyst in step (a) is $H_2SO_4$.

5. The process of claim 1 wherein the reaction is carried out in the presence of a suitable organic solvent.

6. The process of claim 5 wherein the solvent is benzene or chlorobenzene.

7. The process of claim 5 wherein the solvent is acetic acid and a persulfate promoter for reaction in said acid is used.

8. A process for the oxidation of ethyl benzene to form equimolar amounts of vinyl acetate and phenol which comprises:
   (a) oxidizing ethyl benzene with air or oxygen in the liquid phase at temperatures of from 140°-300° C. and at elevated pressures in the presence of a strong acid catalyst, acetic anhydride and a persulfate selected from the group consisting of sodium persulfate, potassium persulfate, persulfuric acid and Caro's dry acid to form phenyl acetate and ethylidene diacetate in approximately equimolar amounts, together with acetic acid;
   (b) separating and recovering acetic acid, phenyl acetate and ethylidene diacetate;
   (c) pyrolyzing said phenyl acetate to form phenol and ketene; and
   (d) pyrolyzing said ethylidene diacetate to form vinyl acetate and acetic acid.

9. The process of claim 8 wherein the acetic acid and ketene are converted to acetic anhydride and recycled to the oxidation step.

10. The process of claim 8 wherein the pressure in step (a) is in the range of from about 50 to 450 psig.

11. The process of claim 8 wherein the acid catalyst in step (a) is $H_2SO_4$.

12. The process of claim 8 wherein the reaction is carried out in the presence of a suitable organic solvent.

13. The process of claim 12 wherein the solvent is benzene or chlorobenzene.

14. The process of claim 12 wherein the solvent is acetic acid.

15. A process for the oxidation of ethyl benzene to form vinyl acetate and phenol which comprises:
(a) oxidizing ethyl benzene with air or oxygen in the liquid phase at temperatures of from 140°–300° C. and at elevated pressures in the presence of a strong acid catalyst, acetic anhydride, molybdenum trioxide and a persulfate selected from the group consisting of sodium persulfate, potassium persulfate, persulfuric acid, and Caro's dry acid to form phenyl acetate and ethylidene diacetate in approximately equimolar amounts, together with acetic acid;
(b) separating and recovering said phenyl acetate and ethylidene diacetate;
(c) pyrolyzing said phenyl acetate to form phenol and ketene; and
(d) pyrolyzing said ethylidene diacetate to form vinyl acetate and acetic acid.

16. The process of claim 15 wherein the acetic acid and ketene are converted to acetic anhydride and recycled to the oxidation step.

17. The process of claim 15 wherein the pressure in step (a) is in the range of from about 50 to 450 psig.

18. The process of claim 15 wherein the acid catalyst in step (a) is $H_2SO_4$.

19. The process of claim 15 wherein the reaction is carried out in the presence of a suitable organic solvent.

20. The process of claim 19 wherein the solvent is benzene or chlorobenzene.

21. The process of claim 19 wherein the solvent is acetic acid.

* * * * *